United States Patent [19]

Holtkamp, Sr.

[11] Patent Number: Plant 7,108

[45] Date of Patent: Jan. 16, 1990

[54] AFRICAN VIOLET PLANT NAMED LITTLE BLUE TOPAZ

[76] Inventor: Reinhold Holtkamp, Sr., Werther Strasse 112, D4294 Isselburg, Fed. Rep. of Germany

[21] Appl. No.: 310,757

[22] Filed: Feb. 15, 1989

[51] Int. Cl.[4] ..... A01H 5/00
[52] U.S. Cl. ..... Plt./69
[58] Field of Search ..... Plt./69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A new and distinct cultivar of African violet named Little Blue Topaz characterized by its miniature growth habit; purplish blue, single violet-shaped flowers; strong stems which curve toward the center to form a compact bouquet above the leaves; profuse and continuous flowering; medium green, spear-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Blue Topaz.

The new cultivar was referred to during the breeding and selection process by the designation Vio ore 87/60 and is a product of a planned breeding program. The new cultivar was originated from a cross made by me in the controlled breeding program in Haffen, Federal Republic of Germany. The female, or seed parent was a cultivar designated 4 Mini. The male, or pollen parent was a cultivar designated H/25/z.

Little Blue Topaz was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Blue Topaz has not been observed under all possible environmental conditions. The phenotype may vary significantly with variations in environment such as temperature, light intensity and day length. The following observations, measurements and values describe the new cultivar as grown in a 4 cm pot in Haffen, West Germany and Nashville, Tenn., under greenhouse conditions which closely approximate those generally used in commercial practice.

The following traits have been repeatedly observed and are determined to be basic characteristics of Little Blue Topaz, which in combination distingush this African violet as a new and distinct cultivar:

(1) Little Blue Topaz will not grow taller than 8 cm.

(2) Single violet-shaped, purplish blue flowers.

(3) Strong wirelike and upright flower stems curving toward the center.

(4) First flash of flowers form a tight bouquet above the leaves.

(5) Profuse flowering; under good growing conditions continuous flowering.

(6) Each plant carries 8–10 and more upright flower stems each of which carries 3–5 and more flowers.

(7) Long lasting, non-dropping flowers.

(8) Plant saleable 10 to 11 weeks after planting of unrooted shoot.

(9) Seed capsules push slightly through.

(10) Medium green, shiny leaves.

(11) Spear-shaped leaves are 1.5 to 3.0 cm in size.

(12) After maturity the flowers dry off, and remain on the peduncle.

The accompanying color photographic drawing shows a typical specimen plant of the new cultivar grown in a 4 cm pot. The plant is pictured next to a pencil, highlighting the miniature size and growth habit of Little Blue Topaz. The colors appearing in the photograph are as true as possible with color illustrations of this type.

In the following description, color references are made to the Royal Horticultural Society Colour Chart (R.H.S.), except where general colors or ordinary significance are referred to. Color values were taken under natural sunlight conditions at approximately 1 p.m. in Nashville, Tenn.

Botanical classification: *Spaintpaulia ionantha,* Ramat., c.v. Little Blue Topaz.

Parentage:

*Male parent.*—H/25/z.

*Female parent.*—4 Mini.

Propagation: The new cultivar holds its distinguishing characteristics through successive propagations by leaf cuttings.

Plant: From 5 cm to 7 cm tall when grown in pots, and approximately 7–10 cm in diameter when fully grown.

*Leaves.*—General form: Spear-shaped. Diameter: 15–20 mm wide and 23–28 mm long. Texture: Leatherlike. Aspect: Shiny, hairy. Veins: Upperside: visible; underside: well pronounced, light green, shiny. Color (upperside): Yellow-Green Group 147 A. Color (underside): Yellow-Green Group 147 D with touches of Greyed-Purple Group 187 A. Young leaves are Greyed-Purple Group 187 A. Petiole: Strong, green, young leaves purplish red, hairy.

*Flowers.*—Buds: Size: 3–4 mm just before opening. Shape: Bell-shaped. Color: Purplish. Sepals: Five (5). Color: Brownish green. Calyx: Shape: Funnel-shaped. Aspect: Spear-shaped, hairy. Peduncle: Character: Strong upright, hairy. Color: Brownish green. Individual flowers: Size: Approximately 25 mm. Shape: Single violet-shaped (3 large, 2 small petals). Color (upperside): Between Violet-Group 87 A and 88 A. Under cooler temperatures and more intensive lighting, the purplish blue tends to intensify. Color (underside): Between Violet-Group 87 B to C and 88 B to C. Borne: Each flower stem carries 3–5 and more flowers on strong, upright peduncles that are free standing above the leaves, thereby forming a compact bouquet. Flowering habit: Flowers 10–11 weeks after planting an unrooted plantlet.

*Reproductive organs.*—Stamens: Two (2). Anthers: 2 composed of 4 anther cells, seed capsule pushes slightly through. Filaments: Yellowish green, 2–3 mm long. Styles: 5–6 mm long, purplish blue, base of ovary light green and hairy.

*Roots.*—Normally developed, white when young, turning slightly brownish when older.

Disease resistance: Good.

General Observations: Little Blue Topaz is a super miniature violet, which does not grow taller than 8 cm. The single violet-shaped flowers are purplish blue contrasting nicely with the bright yellow anthers. The flowers are long-lasting and non-dropping. Occasionally, 1–2 additional very small petals develop in the center. Under good growing conditions Little Blue Topaz will bloom continuously. A nice bouquet of flowers free standing above the medium green, spear-shaped leaves develops approximately 10–11 weeks after planting an unrooted plantlet. Each of the 8–10 and more strong flower stem carriers 3–5 and more flowers.

I claim:

1. A new and distinct cultivar of African violet named Little Blue Topaz, as described and illustrated, and particularly characterized by its miniature growth habit; purplish blue, single violet-shaped flowers; strong stems which curve toward the center to form a compact bouquet above the leaves; profuse and continuous flowering; medium green, spear-shaped leaves; flowering 10–11 weeks after planting of unrooted shoot, and by its long lasting and non-dropping flowers.

* * * * *

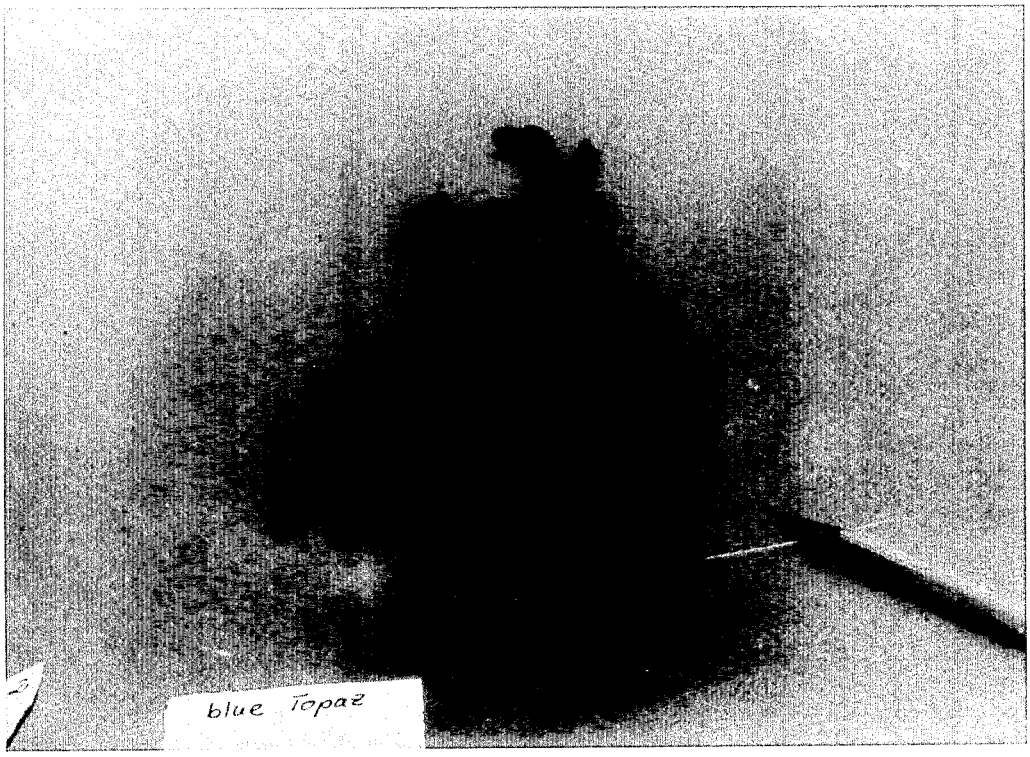
blue Topaz